United States Patent
Wildemeersch

(10) Patent No.: US 10,092,443 B2
(45) Date of Patent: Oct. 9, 2018

(54) COPPER-RELEASING HYBRID IUD WITH ADAPTABLE RETENTION ARM CONNECTED TO FRAMELESS BODY

(71) Applicant: PAT&CO BVBA, Lichtervelde (BE)

(72) Inventor: Dirk Wildemeersch, Ghent (BE)

(73) Assignee: PAT&CO BVBA, Lichtervelde (BE)

( * ) Notice: Subject to any disclaimer, the term of this patent is extended or adjusted under 35 U.S.C. 154(b) by 451 days.

(21) Appl. No.: 14/761,710

(22) PCT Filed: Jan. 17, 2014

(86) PCT No.: PCT/EP2014/050917
§ 371 (c)(1),
(2) Date: Jul. 17, 2015

(87) PCT Pub. No.: WO2014/111533
PCT Pub. Date: Jul. 24, 2014

(65) Prior Publication Data
US 2015/0359663 A1 Dec. 17, 2015

(30) Foreign Application Priority Data
Jan. 17, 2013 (EP) ..................... 13151739

(51) Int. Cl.
*A61F 6/14* (2006.01)
*A61F 6/18* (2006.01)

(52) U.S. Cl.
CPC .............. *A61F 6/144* (2013.01); *A61F 6/142* (2013.01); *A61F 6/18* (2013.01)

(58) Field of Classification Search
CPC . A61F 6/144; A61F 6/142; A61F 6/18; A61K 9/0039; A61K 9/0036; A61M 31/002
See application file for complete search history.

(56) References Cited

U.S. PATENT DOCUMENTS

| | | |
|---|---|---|
| 3,820,535 A | 6/1974 | Marco |
| 4,708,134 A | 11/1987 | Wildemeersch |
| (Continued) | | |

FOREIGN PATENT DOCUMENTS

| | | | |
|---|---|---|---|
| DE | 3209290 A1 * | 12/1982 | ............ A61F 6/144 |
| EP | 0 191 747 A1 | 8/1986 | |
| (Continued) | | | |

OTHER PUBLICATIONS

International Search Report, dated May 28, 2014, from corresponding PCT application.

*Primary Examiner* — Ophelia A Hawthorne
(74) *Attorney, Agent, or Firm* — Young & Thompson

(57) ABSTRACT

A new and improved hybrid "framed-frameless" copper-releasing contraceptive device (IUD) which is a combination of a plastic retention arm of reduced dimensions to adapt to uterine cavities of smaller size, particularly regarding their transverse width at the fundal level of the uterus, and whose retention arm has a centrally located extension of varying length to be connected with hollow copper tubes which functions as the frameless stem of the IUD, and which consists of loosely connected hollow tubes, threaded on a length of suture, or a thin plastic or metallic stem, or a thin polymeric drug eluting stem, allowing release of copper ions, from the outside and from the inside of the tubes, in the uterine cavity thereby enhancing the contraceptive effect, and of which the bottom tube, is crimped onto the lower end of the stem, including a separate metallic ion-releasing fiber, holding all copper tubes together.

23 Claims, 3 Drawing Sheets

(56) References Cited

U.S. PATENT DOCUMENTS

| | | | |
|---|---|---|---|
| 5,494,047 A * | 2/1996 | Van Os | A61F 6/142 |
| | | | 128/832 |
| 2011/0033519 A1 | 2/2011 | Leong | |
| 2012/0318276 A1* | 12/2012 | Wildemeersch | A61K 9/0019 |
| | | | 128/833 |

FOREIGN PATENT DOCUMENTS

| | | |
|---|---|---|
| EP | 0 673 629 A1 | 9/1995 |
| FR | 2 565 482 A2 | 12/1985 |
| WO | 90/09158 A1 | 8/1990 |

\* cited by examiner

COPPER-RELEASING HYBRID IUD WITH ADAPTABLE RETENTION ARM CONNECTED TO FRAMELESS BODY

FIELD AND BACKGROUND OF THE INVENTION

The invention relates to a new and improved combined "framed-frameless" copper-releasing intrauterine contraceptive device (IUD), more particularly to a copper-releasing hybrid IUD with adaptable retention arm connected to frameless body for interval and postpartum contraception, reversible office sterilization and infection prevention.

The known frameless copper intrauterine device, called GyneFix® (EP 0191747) has six copper tubes, each 5 mm long and 2.2 mm wide, threaded on a length of suture material. The proximal end of the device is provided with an anchoring means (knot) for its fixation to the uterine wall in order to prevent that the device is pushed out by the uterus.

Another known device or system is the framed hormone-releasing Femilis® which is T-shaped and of which the retention arm is connected to a longitudinal branch constituting the stem of the T. Similarly an Ω-shaped retention arm has been described which is connected to a similar branch as the T-shaped Femilis hormone-releasing system (IUS, Intra Uterine System), constituting the stem of the device.

The object of the present invention is an intrauterine device of the T-shaped or Ω-shaped type of which the retention arm is connected to a frameless stem consisting only of the active contraceptive substance copper in the form of hollow tubes. This conception is completely different from conventional T-shaped copper IUDs or hormone-releasing IUSs. The majority of these devices are made of a plastic frame overlaid with copper, either copper tubes on the retention arm or a copper wire wound on the stem of the IUD. The present invention is different and serves an important purpose, as will be explained below.

It is indeed very important that women tolerate an IUD to avoid discontinuation of the method. Contraceptives are effective at preventing unintended pregnancy only if women or couples continue to use the method. Many women, particularly the young stop using hormonal methods such as the pill because of side effects. This results often in unplanned pregnancy and induced abortion. For this reason more and more public authorities in developed and developing countries promote and advocate the use of long-acting methods of contraception because they are not dependent on daily motivation and correct and consistent use. IUDs are probably the best methods to help reduce the soaring number of unintended pregnancies because they are long-acting and can easily be inserted and removed. However, most conventional IUDs are too big for many women, particularly the young because the uterine cavity of these women is significant smaller especially when they are less than 25 years of age or even adolescent. Dimensional compatibility of the intrauterine device (IUD) or intrauterine system (IUS) with the uterine cavity leads to high acceptability and continuation of use, a condition to continued use of the method and reduced risk of an unintended pregnancy. Incompatibility, on the other hand, leads to the opposite effect: cramping pain, abnormal or sometimes heavy menstrual bleeding, dislocation/expulsion and pregnancy.

The average width of the uterine cavity at the fundal level in nulliparous women between 15 and 34 years of age is approximately 24 mm (range 20-28 mm). The mean values and standard deviations of the fundal transverse diameter in women with parity one, two or three are only marginally greater. Other studies have found that the uterine volume increases with the presence of menarche, age and parity. Nulliparous and primiparous adolescents younger than 18 years old have a smaller uterine volume than nulliparous and primiparous women 20 to 40 years old.

Most conventional T-shaped IUDs have been invented for use by women with children of which the design and size of the IUD was based on casts made of extirpated uteri. An extirpated uterus has no tonus, contrarily to the uterus in vivo, and, therefore, the casts were too big and not reflective of the true size of a women's uterus. Moreover, the casts were made from extirpated uteri from parous women only. These measurements served as the bases for the development of the conventional T-shaped IUD of which most of them have a span of 32 mm. This span is too big to be comfortable accommodated in the majority of the uterine cavities of most women. Clinical studies conducted with smaller T-shaped devices have shown much better results as far as the occurrence of side effects is concerned. However, as smaller conventional copper IUD have less effective copper surface area, the improvement in comfort and tolerability seen with a reduction of size is sometimes achieved at the expense of the contraceptive effectiveness of the copper-releasing IUD.

The efficacy of a copper IUD depends on the release of copper ions into the uterine cavity and Fallopian tubes. Small amounts of copper have a strong antifertility effect as copper ions are toxic to sperm cells. They inactivate sperm. The greater the amount of copper, the better the protection against pregnancy. High load intrauterine copper devices are more effective than low load copper devices. Furthermore, the effective copper surface area which governs the amount of ions released must also be taken into account. With traditional copper IUDs which utilize copper wire wrapped around a plastic support, the part of the copper lying against the plastic is not exposed to the uterine environment and thus not available as a source of copper ions. Only the exposed surface of the wire is available for copper release and this should be taken into account. It has been calculated that 40% of the copper present on the traditional copper IUDs is not clinically available. The standard prior art "frameless" IUD (GyneFix®) (U.S. Pat. No. 4,708,134 or EP 0191747 incorporated herein by reference) with effective copper surface area of up to 330 mm$^2$ is different than conventional copper wire wrapped IUDs such as the TCu380A IUD (Paragard®). GyneFix is composed of several small copper cylinders threaded on a flexible polymer suture string. The loose copper tubes are open from all sides and all surface areas are in contact with the endometrial environment. Thus, ion release occurs from both the exterior of the tube and also from its interior. As compared to a standard wire wrapped IUD of similar milligram load of copper, the effective surface area for GyneFix is substantially greater. This enhanced surface area and greater availability of copper ions allow for equivalent release rates even when a much smaller device is used. These differences in effective surface area between GyneFix and other copper IUDs explains the high effectiveness of the small frameless copper IUD.

Frameless devices are remarkably well tolerated by any uterus due to the absence of a frame, which eliminates spatial incompatibility with the uterine cavity. Because of its flexibility, embedment of the stem or transverse arm in the uterine wall does not occur, in contrast with conventional IUDs, particularly if the IUD is too big and the stem too long.

The purpose of the present invention therefore is to provide a T- or Ω-shaped copper-releasing IUD of reduced size, remarkably well tolerated, which can easily and safely be inserted, and which has a higher effective copper surface area than conventional and small-size copper IUDs to enhance the contraceptive effectiveness. In addition, by increasing the size of the copper tubes slightly, the lifespan of the IUD will be increased substantially. Long duration of action is important for IUD users as it is economical and may reduce certain health risks (e.g., infection) related to frequent replacement.

This purpose is reached by providing a T- or Ω-shaped IUD, including a longitudinal frameless branch constituting the body or stem of the device; the superior part or transverse arm, constituting the retaining member of the IUD, being linked to the upper part of the frameless body.

Referring to EP673 629 B1 (Van Os), the current application goes much further than the mere description of an IUD with flexible stem and transverse arm.

The current application is a combination of advantageous design elements to which important aspects related to the function as a contraceptive device, are added. These are described below as primary and secondary aims, as well as the further special characteristics of the invention.

SUMMARY OF THE INVENTION

The invention relates to a new and improved hybrid "framed-frameless" copper-releasing contraceptive device (IUD) which is a combination of a plastic retention arm of reduced dimensions to adapt to uterine cavities of smaller size, particularly regarding their transverse width at the fundal level of the uterus. Preferably the retention arm has a centrally located extension of varying length to be connected with hollow copper tubes which functions as the frameless stem of the IUD, and which consists of loosely connected hollow tubes, threaded on a length of suture, or a thin plastic or metallic stem, or a thin polymeric drug eluting stem, allowing release of copper ions, from the outside as well as from the inside of the tubes, in the uterine cavity thereby enhancing the contraceptive effect. The bottom tube is advantageously crimped onto the lower end of the stem, including or not a separate metallic ion-releasing fiber, holding all copper tubes together.

The primary aim of the present invention is to provide a copper-releasing IUD of reduced dimensions in order to enhance tolerance when used in women with smaller-size uterine cavities, which consists of a transverse arm, being retaining member, and a frameless body connected to each other and which constitutes the active part of the IUD.

A device according to the present invention includes a retention arm containing metallic nanoparticles for release of Ag, Au or CuO ions and which is covered by an electro-spun mat which may also containing metallic nanoparticles for additional release of ions for contraceptive purposes and/or infection prevention.

This goal is reached by combining a conventional retention arm, but shorter in length, with the frameless IUD, GyneFix as described in U.S. Pat. No. 4,708,134 or EP 0191747, incorporated herein by reference.

An additional goal is to create a segmented retention arm to allow the tips of the horizontal straight arm to bend in case the fundal transverse diameter is smaller than the length of the retention arm.

An additional goal of the invention is to maximize the release of copper in the upper part of the uterine cavity in the vicinity of the tubal orifices. This goal is reached by adding copper cylinders to the retention arm of the IUD.

The secondary aim of the present invention is to provide a copper IUD which has a smaller total foreign body surface area but a large effective copper surface area, when compared to the effective copper surface area of the high-load conventional copper IUDs in order to create a copper IUD of which the effective copper surface area is almost identical to the nominal surface area. An embodiment of the present invention may have a total copper load is between 300 and 600 mg. The total effective copper surface area is at least 260 to 280 mm$^2$ but preferably over 300 mm$^2$.

This goal is reached, according to one aspect of the present invention, by devising an IUD of small dimensions, wherein the active substance of the non-rigid, flexible stem of the IUD consists only of copper elements, and wherein the components are hollow and solidarized to each other, one behind the other in a non-rigid assembly and wherein the elements are sufficiently short allowing the inner surface of the cylinders to come into contact with the uterine environment.

Another aspect of the invention is to utilize a flexible polymer stem of a diameter substantial smaller than the internal diameter of the copper cylinders. This would allow for the tubes to be freely rotating around the stem, move up and down the stem and allowing access of both external and internal surfaces of the cylinders to the uterine environment. The stem can be inert or be drug eluting. Similarly, the retention arm may or may not be a drug eluting component alone or in combination with a drug eluting stem.

According to another aspect of the invention, the total effective surface area of the IUD is between 200 mm$^2$ and 500 mm$^2$.

According to an additional characteristic of the invention, the effective copper surface area equals the nominal copper surface area which should be at least 300 mm2.

According to yet another aspect of the invention, the components are copper cylinders and are not longer than 6 to 8 mm in order to allow easier direct contact between the inner surface of the cylinders and the uterine environment.

According to yet another characteristic of the invention, the upper copper tube is attached to the middle part of the retention arm; this part being provided with a small longitudinal hole to allow the suture thread, on which the copper tubes are threaded, to pass through the hole and to link the frameless vertical stem or suture of the IUD to the horizontal retention arm.

According to another characteristic of the invention, the tip of the suture thread is heat deformed so that both elements, the retention arm and the stem of the IUD, are firmly secured to each other.

According to yet another characteristic of the invention, the lower copper tube is crimped onto the suture thread or polymer drug fiber to prevent the tubes from sliding off the suture.

According to yet another characteristic of the invention, the hollow elements are separated from each other by a small space to enhance the contact between the inner part of the cylinders and the uterine environment.

According to another characteristic of the invention, the length of the body or stem is no longer than 3.5 cm, preferably only 2.5-3.0 cm.

According to another characteristic of the invention, the horizontal retention arm is preferably not longer than 32 mm but greater than 20 mm to allow the arm to adapt to the transverse dimension of the uterine fundus without causing any damage.

According to yet another characteristic of the invention, the retention arm is provided with thin copper tubes, embedded in the plastic of the retention arm.

Another characteristic of the invention is that the body or stem can be inserted in a thin plastic tube, ready for insertion of the IUD in the uterine cavity. The IUD is simply pushed in the uterine cavity. Whilst the IUD enters the uterine cavity, the flexible retention arm opens to protect against perforation of the uterus which is one of the feared complication of IUD use.

According to an additional characteristic of the invention, the outer diameter of the copper cylinders should not exceed 2.8-3.0 mm to allow easy insertion in the uterus.

According to an additional characteristic of the invention, the inner diameter of the copper cylinders should not be less than 1.0 mm to allow proper copper ion exchange with the uterine environment.

The number of elements may be between 2 and 10, preferably between 3 and 6. Particularly preferred is a structure comprising 5 cylindrical elements, each approximately 5 mm in length, in a row of which the first is linked to the horizontal retention arm and the last has been crimped onto the anchoring thread.

The tertiary aim of the present invention is to provide an IUD which consists of a body as described above but which, in addition, is also provided with an augmented retention means for use in instances where this is needed such as immediately after the delivery of a child when the uterine cavity is greatly extended. Indeed, in the immediate post-partum period, after cesarean section or after normal vaginal delivery, the uterine cavity is still expanded and the insertion of an IUD at that time often results in expulsion of the IUD if no fixation/retention means is provided.

This goal is reached in several ways and will be described in detail below.

DESCRIPTION OF THE DRAWINGS

These and other characteristics of the invention will be more readily understood when referring to the description as well as the accompanying drawings which represent, merely by way of examples, several embodiments of the invention, and in which:

In FIG. 12, the retention arm is covered with an electro-spun mat releasing ions from metallic nanoparticles.

DETAILED DESCRIPTION

Figure 1:
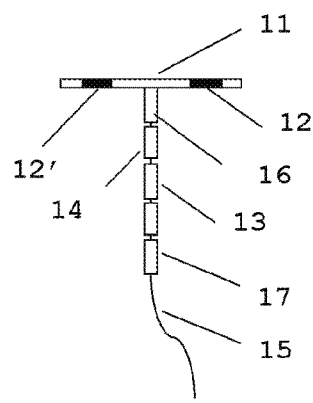
FIG. 1 is a view of the preferred embodiment of the invention having a straight retention arm, provided with two embedded copper cylinders on both sides of the retention arm, connected to frameless body consisting of a succession of hollow copper elements.

Referring now particularly to FIG. 1, a straight horizontal retention arm 11 is made of limited length, preferably no longer that 28 mm, consisting of a semi-flexible material such as polyethylene and which is provided (or not) with two copper tubes 12, 12' embedded on both sides of the retention arm 11 and which is connected in the middle of the retention arm with a frameless body 13 constituting the stem of the IUD which consist of a series of hollow copper tubes 14, threaded on a length of a suture thread 15, of which the top copper tube 16 is connected with a vertical extension (not shown) of the retention arm and which is not longer than the length of the first copper tube, and of which the bottom copper tube 17 is crimped (not shown) on the suture thread. This assembly connects both the horizontal retention arm 11 and frameless stem 13 of the IUD securely together.

Figure 2:
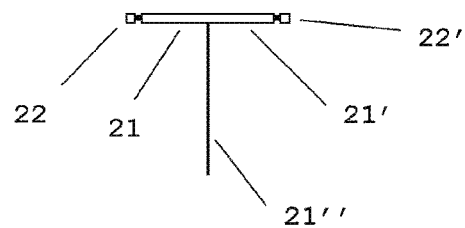
FIG. 2 is another view of the retention arm consisting of three segments, a mid-section and two flexible tips at the ends.

Referring to FIG. 2, the segmented retention arm 21 consists of a mid-section 21' with an extension 21" in the middle and two other segments 22 and 22' at both extremities of the arm that form a flexible connection with the mid-section, for example by a localized narrowing of the material such as polyethylene.

Figure 3:
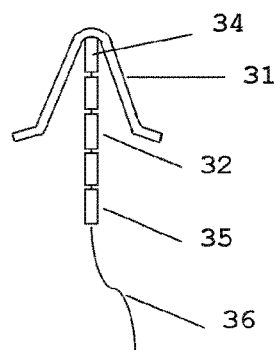
FIG. 3 represents another embodiment of the invention of which the retention arm is Ω-shaped and is connected in a similar way as in FIG. 1.

Referring now particularly to FIG. 3, a curved, Ω-shaped retention arm 31, consisting of a flexible material such as polyethylene and which connected in the middle of the retention arm with a frameless body 32 constituting the stem of the IUD which consist of a series of hollow copper tubes, threaded on a length of a suture thread 33, of which the top copper tube 34 is connected with a vertical extension of the retention arm and which is not longer than the length of the first copper tube, and of which the bottom copper tube 35 is crimped on the suture thread 36. This assembly connects both the retention arm and frameless body of the IUD securely together.

Figure 4:
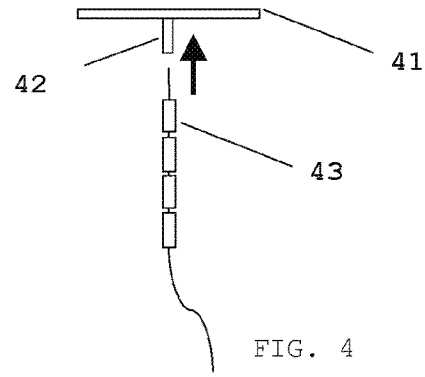
FIG. 4 is a schematic view of realization to connect the T-shaped retention arm with the frameless body or stem of the IUD. The first copper tube is adapted to a plastic extension in the middle of the retention arm which is the preferred embodiment of the T-shaped IUD according to the invention.

Referring to FIG. 4 which is a view of the T-shaped IUD which shows the straight horizontal retention arm 41 with extension 42, and of which the extension adapts, for example by friction, with the upper copper tube 43, and of which the extension is not longer than said tube.

Figure 5:
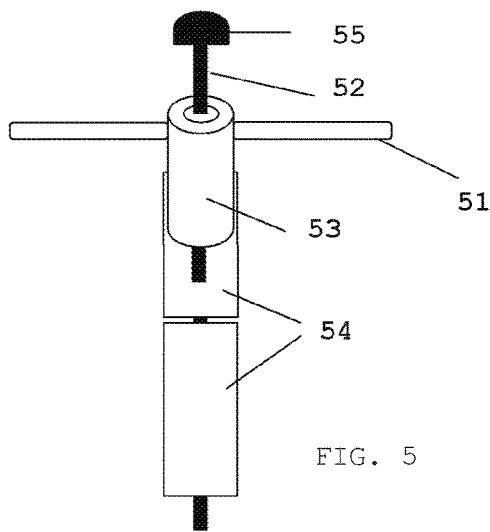
FIG. 5 shows a cross sectional detail of the connection with special reference to the suture which passes through a longitudinal hole in the middle of the extension of the retention arm as well as through the retention arm and connects both the retention arm and the body of the IUD by heat deformation of the tip of the suture so that both parts are secured together.

FIG. 5 is a schematic cross sectional view of the upper end of a T-shaped retention arm 51 with special reference to the suture 52 which passes through a longitudinal hole in the middle of the extension 53 of the retention arm as well as through the retention arm itself and connects both the retention arm and the frameless body of the IUD 54 by heat deformation of the tip 55 of the suture 52 so that both parts are secured together.

Figure 6:
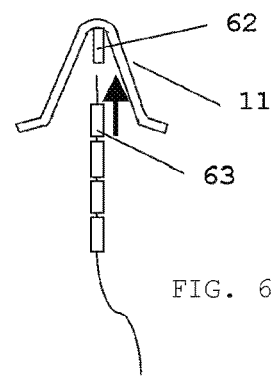
FIG. 6 is another schematic cross sectional view of realization to connect the T-shaped retention arm with the frameless body or stem of the IUD. The first (proximal) copper tube is fixed on a plastic extension in the middle of the retention arm which is the preferred embodiment of the Ω-shaped IUD according to the invention.

Referring now to FIG. 6 which is another schematic view of the Ω-shaped retention arm 61 with extension 62, and of which the extension adapts, for example by friction, with the upper copper tube 63 and which is not longer than said tube.

Figure 7:
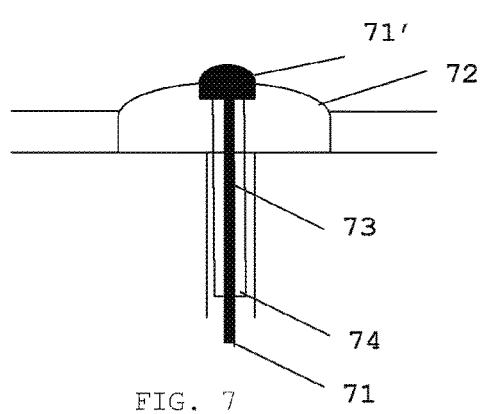
FIG. 7 shows a cross sectional detail of the connection with special reference to the suture which passes through a hole in the middle of the T- or Ω-shaped retention arm and connects both the retention arm and the body of the IUD by heat deformation of the tip of the suture so that both parts are secured together.

FIG. 7 is a cross sectional view of the upper end of the suture 71 which is heat deformed forming a spherical or mushroom-shaped body 71' which is embedded in a small protruding part 72 made in the upper part of the mid-section of the retention arm. The longitudinal hole 73 in extension 74 is illustrated.

Figure 8:
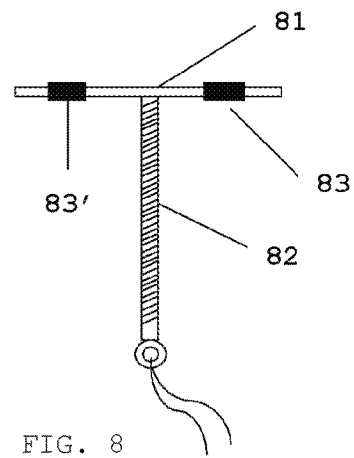
FIG. 8 shows the conventional T-shaped TCu380A IUD which has a plastic frame on which copper is added: a copper wire on the stem of the IUD and copper tubes on the retention arm. The horizontal arm is 32 mm long and the vertical stem 36 mm.

FIG. 8 shows the difference between the IUD according to the invention and the standard conventional TCu380A IUD. The retention arm 81 of the TCu380A as well as the stem 82 are significantly longer. Furthermore the stem is semi-rigid whilst with the IUD according to one aspect of the invention the body is completely flexible. In addition, the copper wire of the TCu380A is not hollow and the part of the wire against the plastic frame does not release copper ions. The copper collars 83 and 83' on the retention arm are superimposed and not embedded in the plastic frame. The total effective copper surface area of 254 mm$^2$ is significantly smaller.

Figure 9:
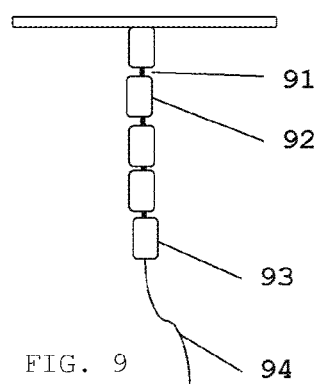
FIGS. 9 and 10 show another representation of the invention whereby the copper tubes are threaded on a very thin stem that can be drug eluting. The copper tube are kept in place by crimping the lower copper tube on the stem (FIG. 9) or by a molded part that is large enough to prevent the tube from sliding off the stem (FIG. 10). In one embodiment of the invention, an additional copper or stainless steel, gold, or silver wire or spiral is provided, running through the inner side of the loose copper tubes and is affixed in a central hole in the extension of the retention arm.

FIG. 9 a further embodiment according to the invention whereby on the thin and flexible plastic stem 91 of the framed IUD copper tubes 92 are assembled which can freely move to allow contact with the endometrial milieu and of which the lower copper tube 93 is crimped (not shown) onto the stem to avoid the copper tubes to slide off the stem and also affixes a tail 94 for removal of the IUD.

Figure 10:
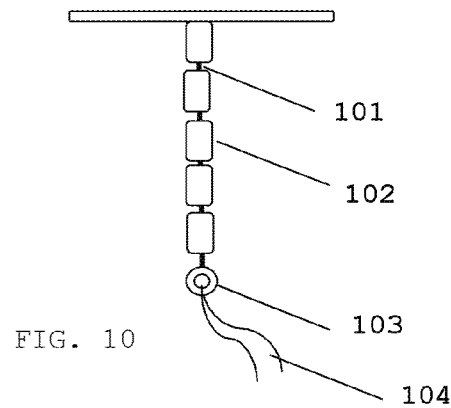

FIG. 10 is still a further embodiment according to the invention whereby, on the thin and flexible plastic stem 101 of the framed IUD, copper tubes 102 are assembled which can freely move to allow contact with the endometrial milieu and of which the lower end of the stem is provided with a thickening of the stem 103 to avoid the copper tubes to slide off the stem and to which a tail 104 can be tied for the removal of the IUD.

Figure 11:
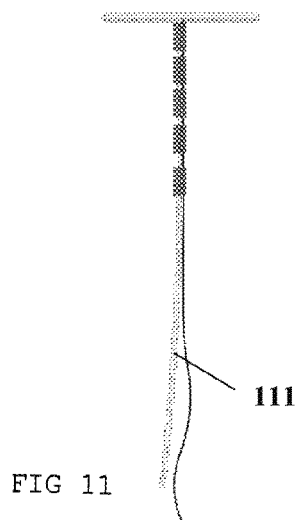
FIGS. 11 and 12 show the devices having an additional drug eluting tail for infection prevention.

FIG. 11 shows an additional particularity of the invention in which a second tail of the IUD consists of a metallic nanoparticle containing polymeric drug delivery system 111 covered by a outer layer consisting of a loaded electro-spun fiber mat.

Figure 12:
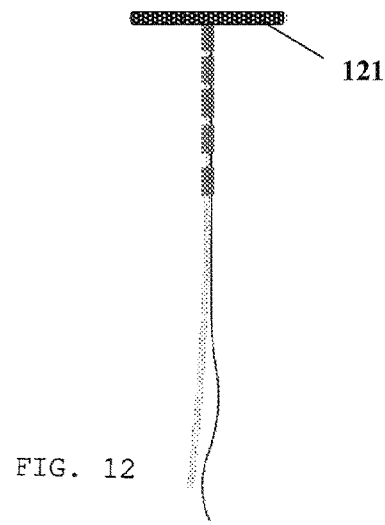

FIG. 12 shows yet an additional particularity of one aspect of the invention in which a transverse arm of the IUD consists of plain plastic or of a metallic nanoparticle containing polymeric drug delivery system 121 covered by a outer layer consisting of a loaded electro-spun fiber mat.

Figure 13:
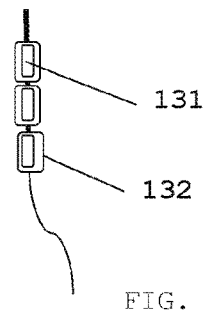
FIGS. 13 an 14 are modes of realization that are similar to the figures in FIGS. 9 and 10 with this difference that the active substance consists of inner and outer copper tubes (FIG. 13) which can freely move independent from each other to increase the effective copper surface area without increasing the total foreign body surface area to limit the impact on menstrual blood loss. The stem in FIG. 14 is covered by a metallic nanoparticle-loaded ion-eluting segment at the inside of the copper tubes. The retention arm can be T- or Ω-shaped (not shown).

FIG. 13 is still a further embodiment according to the invention whereby the stem consists of a series of inner copper tubes 131 and outer copper tubes 132.

Figure 14:
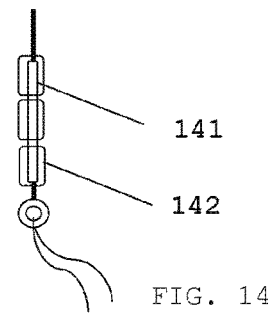

FIG. 14 is still another embodiment according to the invention whereby the stem consists of an inner polymer loaded with metallic or other nanoparticles 141 and a series of outer copper tubes 142.

Figure 15:
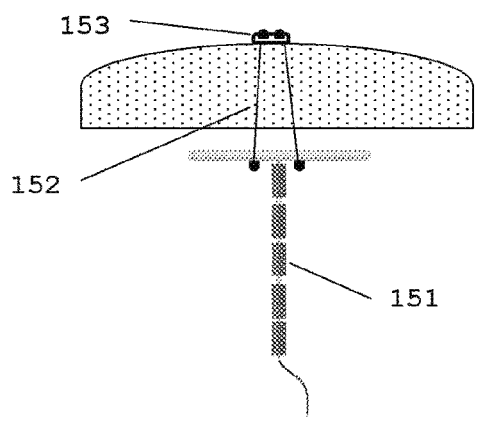
FIG. 15 are modes of realization for the retention of the IUD according to the invention whereby, the IUD is suspended by sutures transfixed through the fundus of the uterus and attached using biodegradable material on the surface of the uterus. When the uterus has regained its normal size, the biodegradable material will have been absorbed, leaving only the transverse arm of the IUD to retain it in the involuted uterine cavity.

FIG. 15 shows a mode of realization for the retention of the IUD according to the invention whereby, the IUD 151 is suspended by sutures 152 transfixed through the fundus of the uterus and attached using biodegradable material 153 on the surface of the uterus.

Figure 16:
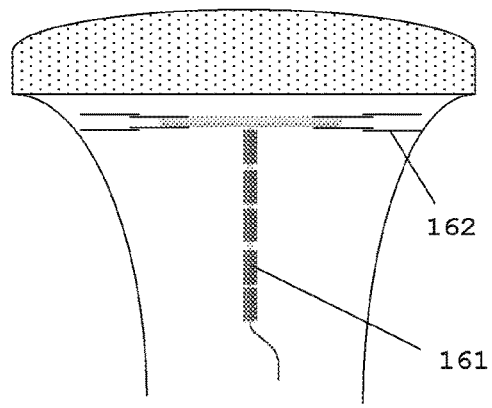
FIG. 16. Is a similar situation as in FIG. 15. However, the IUD is not suspended with a suture(s) but by biodegradable extensions of the transverse arm that are foldable when the involuting muscle pushed the tube-shape extensions towards the midline before being absorbed completely.

FIG. 16. The IUD 161 in FIG. 16 is not suspended with a suture(s) but by biodegradable extensions 162 of the transverse arm that are foldable as a consequence of pressure of the muscle when the uterus becomes smaller.

The invention discloses, separately or in combination the following various additional features that can be applied to the devices as claimed.

A "T" or "Ω" shaped intrauterine device wherein the stem of the framed IUD is between 0.3 and 1.2 mm in diameter on which copper tubes are assembled that can freely move to allow contact with the endometrial milieu and of which the lower copper tube is crimped onto the stem to avoid the copper tubes to slide off the stem and also contains a tail for removal of the IUD.

According to another aspect, a lower end of the stem of the framed IUD is provided with a thickening to avoid the copper tubes to slide off the stem and to which also a tail is tied for removal of the IUD.

According to still another aspect the shape of the tubes can be cylinders, spheres, egg-shaped, prism, square, triangular or any geometric design with a hollow core to allow contact with endometrial fluids and release ions from multiple surfaces.

The stem may consist of a double copper tube system, of which both can freely move independently from each other, in order to increase the copper surface area.

The frameless or framed IUD of which the stem consists of a double tube system of which the inner tube is a polymeric copper or copper oxide, or other noble metal nanoparticle ion release system, surrounded by freely moving copper tubes.

A frameless/framed IUD which is provided with a means whereby the IUD is suspended by suture that fix the IUD through the entire wall of the uterine fundus and which are secured temporarily to a biodegradable body on the surface of the uterus.

The transverse arm is provided with foldable, biodegradable extensions that prevent downward displacement and expulsion of the IUD.

The invention has been described and illustrated merely by way of examples which are in no way restrictive. Numerous changes in its conception may be made without departing from the spirit of the invention.

The invention claimed is:

1. A framed-frameless, copper-releasing contraceptive device, said device comprising:
   a flexible plastic stem, an outside diameter of said stem being between 0.3 and 1.2 mm;
   a flexible plastic retention arm connected to said stem;
   hollow, copper tubes loosely threaded about said stem, said copper tubes comprising a proximal copper tube and a distal copper tube,
   wherein said stem has the outside diameter sufficiently smaller than an internal diameter of the copper tubes to allow release of copper ions from an outside as well as from an inside of the copper tubes, the copper tubes being freely rotatable around the stem, the copper tubes being freely movable up and down the stem; and
   an extension centrally provided on the retention arm, said extension being provided with the proximal copper tube of said stem.

2. The device according to claim 1, wherein an effective copper surface area of said device is 260 to 280 mm².

3. The device according to claim 2, wherein said extension is no longer than a length of said proximal copper tube.

4. The device according to claim 1, wherein said proximal copper tube and said extension frictionally engage.

5. The device according to claim 1, wherein said proximal copper tube is crimped onto said extension.

6. The device according to claim 1, wherein said extension is no longer than a length of said proximal copper tube.

7. The device according to claim 1, wherein the copper tubes are separated from each other.

8. The device according to claim 1, wherein a lower end of said stem is provided with a thickening portion that keeps the copper tubes from sliding off said stem, and further comprising a tail tied to the lower end of said stem, the tail being for removal of said device.

9. The A device according to claim 1, wherein said retention arm and said stem constitute a frame of the device.

10. The device according to claim 1, wherein a length of the retention arm is no longer than 28 mm.

11. The device according to claim 1, wherein the retention arm is multi-segmented and thereby adaptable to different sizes and volume changes of a uterine cavity.

12. The device according to claim 1, wherein the retention arm contains metallic nanoparticles for release of Ag, Au or CuO ions and the retention arm is covered by an electro-spun mat.

13. The device according to claim 1, wherein the retention arm contains metallic nanoparticles for release of Ag, Au or CuO ions and the retention arm is covered by an electro-spun mat also containing the metallic nanoparticles for additional release of ions for contraceptive purposes and/or for infection prevention of infections.

14. The device according to claim 1, wherein the distal copper tube is crimped onto the stem, the distal copper tube being crimped onto the stem holding all the copper tubes together.

15. The device according to claim 1, further comprising a tail for the removal of the device, the tail comprising a drug-eluting, semi-rigid fiber which is comprised of a combination of metallic nanoparticle-containing material and electro-spun polymeric material, thereby releasing ions from metallic nanoparticles.

16. The device of claim 1, wherein the device has a total copper load between 300 and 600 mg.

17. The device according to claim 1, wherein said retention arm is Ω-shaped.

18. The device according to claim 1, wherein the stem is made of polypropylene.

19. The device according to claim 1, further comprising additional copper cylinders embedded on both sides of the retention arm.

20. The device according to claim 1, further comprising an additional copper, stainless steel, gold, or silver wire or spiral running through an inner side of the loosely threaded copper tubes and affixed in a central hole in said extension of the retention arm.

21. The device according to claim 1, wherein,
   the device comprises exactly one stem and exactly one arm,
   the extension centrally provided on the retention arm is located transverse to the retention arm,
   the one stem is secured to the extension, thereby extending from a middle of the one arm, the one arm being transverse to the one stem.

22. A T- or Ω-shaped intrauterine device comprising:
   a frameless stem having a diameter of between 0.3 and 1.2 mm;
   a retention arm connected to said stem; and
   two copper tube systems provided on said stem, each of said copper tube systems freely movable independently from each other copper tube system, each said copper tube system having copper tubes that are freely movable to allow contact with an endometrial milieu, the copper tube systems being freely rotatable around the stem, the copper tubes freely movable up and down the stem,
   wherein a distal one of the copper tubes of each system is crimped onto said stem to prevent the copper tubes from sliding off said stem; and
   a tail for removal of the device.

23. The device according to claim 22, wherein a lower end of said stem is provided with a thickening portion that keeps the copper tubes from sliding off said stem, and the tail is tied to the lower end of said stem, the tail being tied to the thickening portion.

* * * * *